United States Patent [19]

Kurz

[11] 4,337,037
[45] Jun. 29, 1982

[54] FIXED LINGUAL ORTHODONTIC APPLIANCE FOR THE MAXILLARY ARCH

[76] Inventor: Craven H. Kurz, No. 6 N. Star, Apt. 106, Marina del Rey, Calif. 90291

[21] Appl. No.: 256,961

[22] Filed: Apr. 23, 1981

Related U.S. Application Data

[63] Continuation-in-part of Ser. No. 120,146, Feb. 11, 1980, abandoned.

[51] Int. Cl.³ .................................................. A61C 3/00
[52] U.S. Cl. ........................................... 433/8; 433/9
[58] Field of Search ..................... 433/8, 9, 10, 11, 12, 433/13, 14, 15, 16, 17, 24

[56] References Cited

U.S. PATENT DOCUMENTS

| | | | |
|---|---|---|---|
| 1,622,856 | 3/1927 | Angle | 433/8 |
| 2,267,073 | 12/1941 | Boyd | 433/15 |
| 3,605,233 | 9/1971 | Rosiello | 433/8 |
| 3,842,503 | 10/1974 | Wildman | 433/24 |
| 3,922,787 | 12/1975 | Fischer et al. | 433/15 |
| 4,209,906 | 7/1980 | Fujita | 433/11 |
| 4,216,583 | 8/1980 | Reynolds | 433/17 |

*Primary Examiner*—Gene Mancene
*Assistant Examiner*—John J. Wilson
*Attorney, Agent, or Firm*—Keith D. Beecher

[57] ABSTRACT

A direct-bonded fixed lingual orthodontic appliance is provided which comprises a plurality of metal or plastic brackets and tubes, which are designed to be cemented directly to the lingual surfaces of the teeth of the maxillary arch, and an arch wire extending around the lingual side of the arch intercoupling the brackets and tubes. The brackets are made with smooth angles and low profile to prevent irritation to the tongue, and to assure that the action of the tongue will not be impeded in any way. The base of each bracket is shaped to adapt it to the normal lingual surface of the corresponding tooth so as to provide good retention. An edgewise transverse slot is provided in each bracket with the proper buccolingual depth, mesio-distal tips and occlusal root torques to provide an appliance which accepts a smooth curved arch wire with the only in-and-out bend requirement being between the bicuspids and first molars. To allow ease of arch wire placement, the slot of the first molar bracket, and the mesial end of the second molar tube each has a funnel shape. A bite plane is incorporated in the anterior brackets to prevent the brackets from being sheared off in occlusal contact.

7 Claims, 17 Drawing Figures

(10B IS MIRROR IMAGE)

TORQUE: +68°
ANGULATION: +5°
ROTATION: 0°
IN-OUT: ∅
SLOT SIZE: .018
PAD: SPECIAL LINGUAL DESIGN (12B IS MIRROR IMAGE)

TORQUE: 58°
ANGULATION: +9°
ROTATION: 0
IN-OUT: 0
SLOT SIZE: .018
PAD: SPECIAL LINGUAL DESIGN (14B IS MIRROR IMAGE)

TORQUE: +55
ANGULATION: +12
ROTATION: + 4
IN-OUT: .010
SLOT SIZE: .018
PAD: SPECIAL LINGUAL DESIGN

FIG. 5A
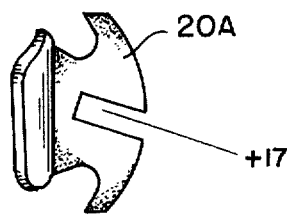
(20B IS MIRROR IMAGE)
FIG. 5B
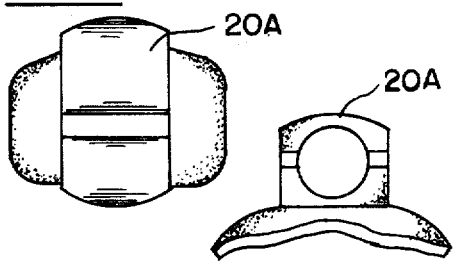
FIG. 5C
| TOOTH | UPPER 1ST & 2ND BICUSPID |
|---|---|
| TORQUE | +17 |
| TIP | 0 |
| ROTATION | −4 |
| IN-OUT | THIN BASE |
| SLOT SIZE | .018 |
FIG. 6A
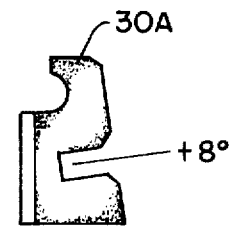
UPPER 1ST MOLAR
TORQUE ANGLE: +8°
TIP ANGLE 0°
ROTATION: 0
IN-OUT: THIN BASE
SLOT SIZE .018
FIG. 6B
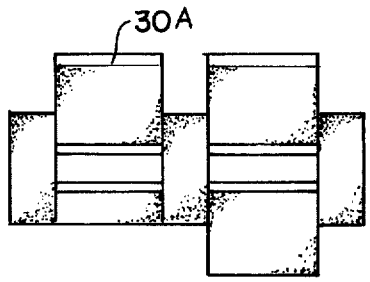
(30B IS MIRROR IMAGE)
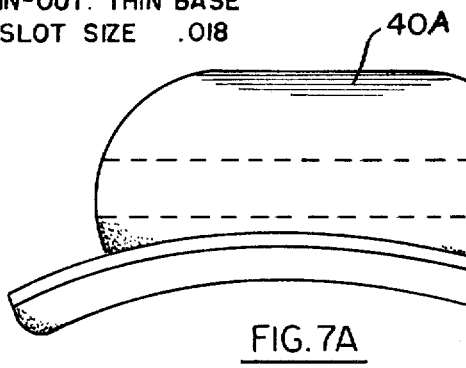
FIG. 7A
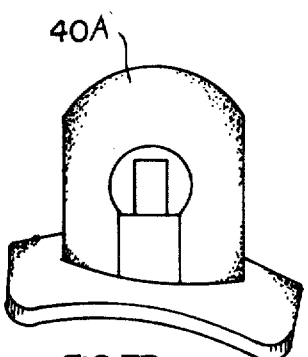
FIG. 7B
| TOOTH | TORQ. ANGLE | TIP ANGLE | ROTATION |
|---|---|---|---|
| UPPER 1ST MOLAR | +8° | 0° | 0 |
| UPPER 2ND MOLAR | +12° | 0° | 0 |

FIXED LINGUAL ORTHODONTIC APPLIANCE FOR THE MAXILLARY ARCH

This application is a continuation-in-part of copending application Ser. No. 120,146, filed Feb. 11, 1980, now abandoned.

BACKGROUND OF THE DISCLOSURE

The prior art fixed orthodontic appliances usually comprise a plurality of brackets and tubes which are cemented or banded to the labial and buccal surfaces of the respective teeth around the arch, and which are intercoupled by an arch wire extending around the external surface of the arch. Although the prior art appliances are effective, they are unsightly and embarrassing to the wearer.

The direct bonded orthodontic appliance of the present invention includes brackets and tubes which are designed to be cemented to the lingual surfaces of the teeth of the maxillary arch, so as to be virtually invisible. The appliance of the invention finds utility in the correction of the maxillary arch, where aesthetics are important to the wearer.

The appliance of the invention has the following advantages:

1. It is invisible to public view making it the most aesthetic appliance available.
2. It can perform all the necessary requirements of a fixed orthodontic appliance, such as:
   a. Translation of crowns and roots of the maxillary teeth to a desired position;
   b. Act as a bite opening means to accomplish the opening of a deep anterior bite situation so as to aid in the immediate relief of an over closed occlusion which is causing temporomandibular problems;
   c. Aid in the anterior advancement of lingually inclined maxillary anteriors, such as found in the Class II Division II deep bite malocclusions.

The brackets of the appliance of the invention may be all metal, part metal and part plastic, or all plastic.

BRIEF DESCRIPTION OF THE DRAWINGS

FIGS. 4A, 4B and 4C are three views of a maxillary lingual bracket suitable for use on the lingual surfaces of the cuspids;

FIGS. 5A, 5B and 5C are three views of a maxillary lingual bracket suitable for use on the lingual surfaces of the bicuspids;

FIGS. 6A and 6B are two views of a maxillary lingual bracket suitable for use in the lingual surfaces of the first molars; and FIGS. 7A and 7B are two views of a maxillary lingual tube suitable for use on the lingual surfaces of the first and second molars.

DETAILED DESCRIPTION OF THE ILLUSTRATED EMBODIMENT

The bases of the lingual maxillary brackets of the invention incorporate the straight wire concept by providing an individualized thickness for the brackets so that a straight contoured arch wire will not require in and out bends, as it is inserted into the edgewise transverse slots of the brackets. The brackets, moreover, may incorporate a built-in angulation mesio-distally, and a built-in angulation bucco-lingually and labio-lingually.

Figure 1:
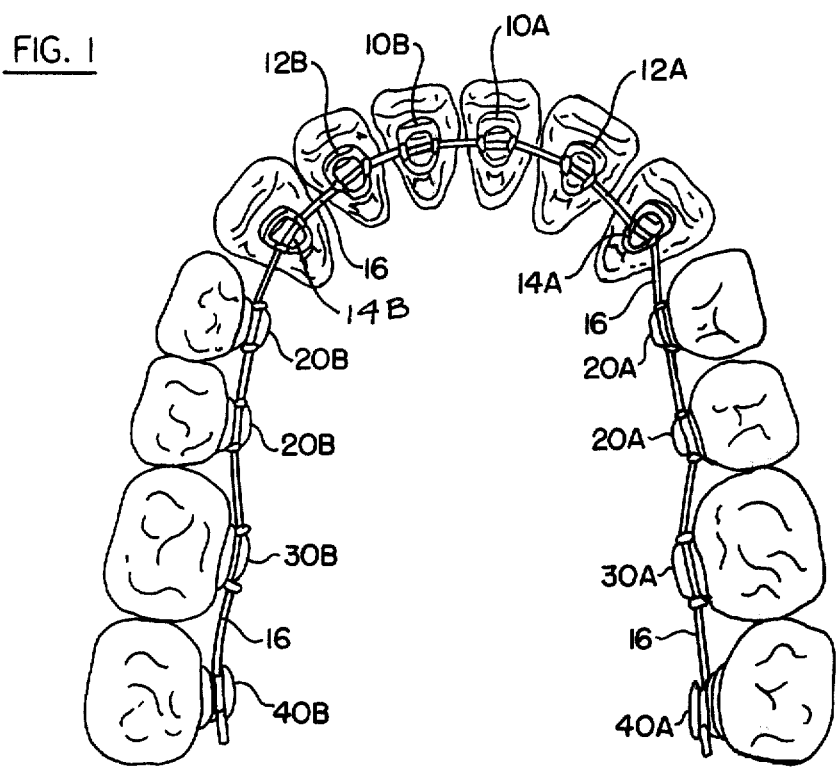
FIG. 1 is a plan view of the maxillary arch, and showing a direct bonded fixed lingual orthodontic appliance, representative of one embodiment of the invention, in place on the lingual surfaces of the teeth forming the arch.

In the representation of FIG. 1, a direct bonded fixed lingual orthodontic appliance, constructed in accordance with one embodiment of the invention, is shown with its brackets and tubes adhesively attached to the lingual surfaces of the teeth forming the illustrated maxillary arch.

The orthodontic appliance of FIG. 1 includes brackets 10A, 10B, 12A, 12B, 14A, 14B, 20A, 20B, 30A and 30B; and tubes 40A and 40B. The brackets and tubes are adhesively attached to the lingual surfaces of the central incisors, the lateral incisors, the cuspids, the bicuspids, and the first and second molars of the maxillary arch of FIG. 1.

Figure 2A:
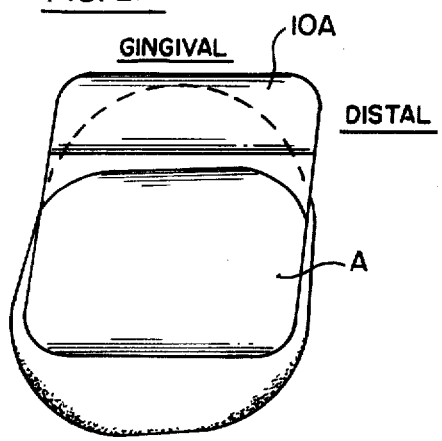
FIGS. 2A, 2B and 2C are three views of a maxillary lingual bracket suitable for use on the lingual surfaces of the central incisors of FIG. 1.
Figure 2B:
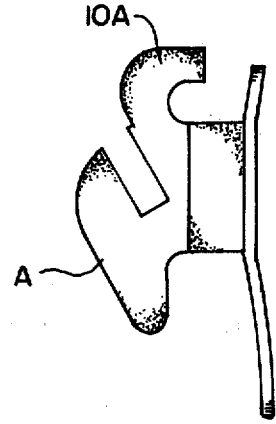
Figure 2C:
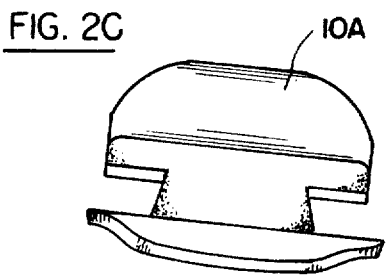
Figure 3A:
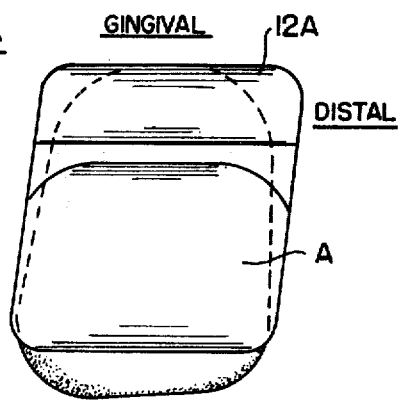
FIGS. 3A, 3B and 3C are three views of a maxillary lingual bracket suitable for use on the lingual surfaces of the lateral incisors.
Figure 3B:
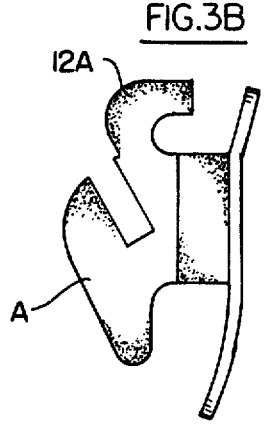
Figure 3C:
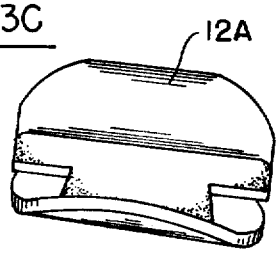
Figure 4A:
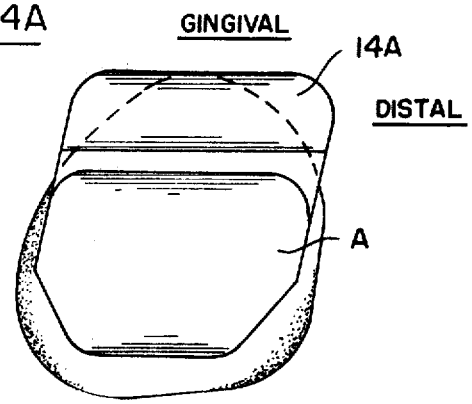
Figure 4B:
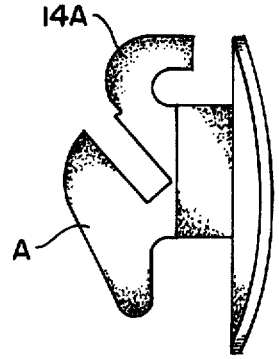
Figure 14C:
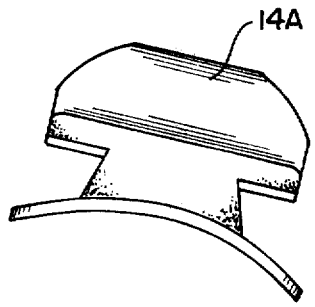

The design of the brackets of the maxillary central incisors, lateral incisors, and cuspids is essentially the same, as shown in FIGS. 2A, 2B, 2C; 3A, 3B, 3C; and 4A, 4B, 4C. As illustrated, the external edges of the brackets are rounded to avoid trauma to the tongue. There are no sharp corners, and in each instance, the bracket profile is kept intentionally low to avoid crowding the tongue space. Also, each bracket includes an inclined bite plane "A" so that the incisal edges of the corresponding mandibular teeth will not tend to shear the brackets off the maxillary teeth when they contact the bracket. In each case, as the mandibular incisor bites against a maxillary bracket, the force direction is such that the bracket is forced against the lingual surface by the occlusal force, and there is no tendency to shear the brackets off the teeth.

The bases of the anterior maxillary brackets 10A, 10B, 12A, 12B, 14A and 14B for the maxillary central, lateral and cuspid incisors are formed to seat into the respective lingual surfaces of the maxillary anterior teeth. The base of each bracket is convex mesial/distally to fit into the marginal ridges of the teeth. The gingival portion of each of the brackets is tapered to conform with the gingival taper of the corresponding tooth. The brackets are designed to fit between the lingual ridges of the teeth in intimate contact with the lingual tooth surface. This shaping of the brackets allows for optimal bonding of the brackets to the teeth, and for a uniform fit of the brackets onto the lingual surfaces of the teeth. The gingival edges of the anterior brackets are contoured to fit over the lower margin of the cingulum area of the teeth.

Each of the anterior maxillary brackets 10A, 10B, 12A, 12B, 14A and 14B, (as shown in FIGS. 2A, 2B, 2C; 3A, 3B, 3C, and 4A, 4B, 4C) includes a base portion which is adhesively attached to the lingual surface of the tooth by an adhesive layer. The shaping of each of the anterior maxillary brackets is such that it assures a uniform fit of each bracket onto the lingual surface of the corresponding tooth so that the torque and angulation cut into the slope of the edgewise transverse slot in each bracket will be accurately translated to the tooth. The base of each of the brackets is of a thickness such that no in-and-out bends are required in a contoured straight arch wire. As described above, each of the brackets are also provided with an angled bite plane "A" to prevent the mandibular teeth from shearing off the brackets.

The orthodontic appliance of the invention also includes brackets 20A, 20B for the first and second bicuspids, brackets 30A, 30B for the first molars, and tubes 40A, 40B for the second molars, as shown in FIGS. 5A, 5B, 5C; 6A, 6B; and 7A, 7B.

The edgewise slots of brackets 30A, 30B are made larger on their lingual surface, and they taper to their proper slot size as the depth of the slot is reached so as to create a funnel effect to allow ease of placement of the arch wire. Likewise, the mesial end of each of the tubes 40A, 40B for the second molars has a larger opening, likewise, to create a funnel effect for ease of arch wire placement.

The illustrated lingual orthodontic appliance is a complete straight wire appliance from the second molar 40A on one side of the upper arch to the second 40B molar on the opposite side of the arch, with the only wire bends occurring between the cuspids and bicuspids. The lingual appliance in one embodiment may be provided with no built-in labial/lingual or buccal/lingual torquing feature, and with no built-in mesio/distal tip or angulation feature. In another embodiment, the lingual appliance of the invention may be provided that has all the built-in requirements of a straight wire appliance, specifically, standardized built-in base thickness so that no in-and-out bends are required of the arch wire, built-in labial/lingual and buccal/lingual torquing features, and built-in mesio/distal angulation capabilities, as illustrated.

As mentioned above, the brackets of the invention may be all-metal, all-plastic or part-metal and part-plastic. The all-metal bracket has the advantage of being the strongest design, and the metal arch wire moves with less friction in a metal slot reducing any drag and loss of efficiency during orthodontic movements. The metal bracket must have a perforated base, or be provided with a screen attached to the base, so that it can be adhesively attached to the tooth surface. The all-plastic appliance is not as strong as the all-metal appliance, but it provides a better chemical bond to the tooth surface. To achieve maximal adhesion, it is desirable to combine the chemical bond of the adhesive with some mechanical retention, and this may be achieved by providing perforations in the plastic base.

The provision of metal brackets and tubes with plastic base is desirable since chemical bonding of the adhesive and the base may be achieved for maximal adhesive strength, whereas the strength of the metal brackets and tubes is maximal. Also, as mentioned above, there is a greater ease of arch wire movement in the metal slot reducing friction drag of the arch wire during orthodontic movements. The metal brackets and tubes also provide accurate translation of the angulation and torque to the teeth.

Brackets and tubes which are part metal and part plastic are the most aesthetic, may be adhesively attached to the teeth with a chemical bond for maximum strength including a metal part which translates the torque and tip accurately to the teeth, and gains strength from the metal so as to prevent breakage from occlusal trauma. The metal part of the slot increases the efficiency of the orthodontic movement for the metal arch wire since the wire slides better against the metal. The all-metal bracket with a metal screen base has the advantage of strength to withstand occlusal trauma. The mechanical bond of the screen base is sufficient to hold the all-metal bracket in a firm adhesive bond with the tooth.

Although particular embodiments of the invention have been shown and described, modifications may be made. It is intended in the claims to cover the modifications which come within the spirit and scope of the invention.

What is claimed is:

1. A lingual orthodontic appliance for the teeth of the maxillary arch comprising: a bracket shaped to fit between the lingual ridges of a particular tooth of the maxillary arch and shaped to fit the anatomy of the lingual surface of the particular tooth, and to be positioned over the cingulum area, the bracket having a slot extending mesiodistally for receiving an arch wire, and said bracket having an inclined bite plane formed on the lingual surface thereof in position to be engaged by the corresponding tooth of the mandibular arch and having a selected inclination such that as the corresponding tooth bites against the bite plane the resultant force direction is such that the bracket is forced against the lingual surface of the particular tooth by the occlusal force, so as to prevent the bracket from being sheared off the particular tooth by the corresponding mandibular tooth.

2. The lingual orthodontic appliance defined in claim 1, in which the bracket is adapted to be adhesively bonded to the lingual surface of the tooth.

3. The lingual orthodontic appliance defined in claim 2, in which the bracket has rounded edges and corners to obviate trauma to the tongue.

4. The lingual orthodontic appliance defined in claim 2, in which the bracket has a base which is convex gingivally and straight incisally.

5. The lingual orthodontic appliance defined in claim 2, in which the bracket has a base which is convex mesiodistally to fit into the marginal lingual ridges of an anterior tooth.

6. The lingual orthodontic appliance defined in claim 1, in which the slot is configured to accept a smooth curved arch wire.

7. The lingual orthodontic appliance defined in claim 1, in which the gingival edge of the bracket is contoured to fit around the incisal margin of the cingulum area.

* * * * *